United States Patent [19]

Woo

[11] 4,421,929

[45] Dec. 20, 1983

[54] TETRACARBOXYLIC ACIDS

[75] Inventor: Edmund P. Woo, Midland, Mich.

[73] Assignee: The Dow Chemical Company, Midland, Mich.

[21] Appl. No.: 326,717

[22] Filed: Dec. 2, 1981

Related U.S. Application Data

[63] Continuation-in-part of Ser. No. 113,896, Jan. 21, 1980, abandoned, which is a continuation-in-part of Ser. No. 53,672, Jul. 2, 1979, abandoned.

[51] Int. Cl.³ .................... C07C 59/00; C07C 65/00
[52] U.S. Cl. .................... 562/465; 562/433; 562/434; 562/426; 562/427; 562/466; 562/467; 562/468; 562/488; 562/489; 562/490; 562/492
[58] Field of Search .............. 562/490, 492, 489, 488, 562/468, 433, 434, 465, 426, 427, 466, 467

[56] References Cited

U.S. PATENT DOCUMENTS

| | | | |
|---|---|---|---|
| 2,047,398 | 7/1936 | Voss | 562/434 |
| 2,913,482 | 11/1959 | Dazzi | 562/433 |
| 3,322,829 | 5/1967 | Zienty | 562/427 |
| 3,420,870 | 1/1969 | Zienty | 562/427 |
| 3,468,940 | 9/1969 | Zienty | 562/427 |

FOREIGN PATENT DOCUMENTS

| | | | |
|---|---|---|---|
| 6603419 | 9/1966 | Netherlands | 562/434 |
| 6603420 | 2/1967 | Netherlands | 562/434 |
| 770222 | 3/1957 | United Kingdom | 562/433 |

OTHER PUBLICATIONS

Royals, E. E., Advanced Org. Chem., Prentice Hall, 798–799, (1961).

*Primary Examiner*—Paul J. Killos
*Attorney, Agent, or Firm*—Douglas N. Deline

[57] ABSTRACT

Novel tetracarboxylic acids are described of the formula

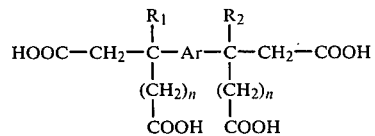

wherein Ar, $R_1$ and $R_2$ are named substituents, and both n's are zeros or ones.

8 Claims, No Drawings

TETRACARBOXYLIC ACIDS

CROSS-REFERENCE TO RELATED APPLICATION

This is a continuation-in-part of my copending application Ser. No. 113,896, filed Jan. 21, 1980 which is a continuation-in-part of my copending application Ser. No. 053,672, filed July 2, 1979 both now abandoned.

BACKGROUND OF THE INVENTION

The invention relates to new chemical compounds and particularly to derivatives of aromatic dicarbonyl compounds. These derivatives, more specifically are tetracarboxylic acid derivatives of aromatic dicarbonyl compounds and exhibit utility as synthetic resin intermediates.

DESCRIPTION OF THE PRIOR ART

U.S. Pat. Nos. 3,293,278 and 3,355,464 teach certain derivatives of diphenylethylbenzene, specifically derivatives of the formula

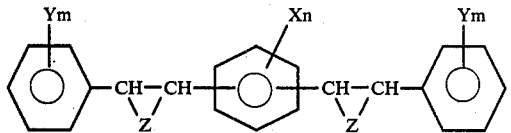

wherein Z is a divalent moiety including

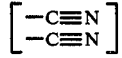

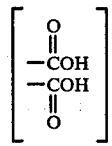

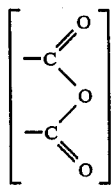

V. V. Perekalin et al. in J. Gen. Chem. USSR, Eng. Ed., 28, 1861 (1958) disclosed the synthesis of certain bis(nitroalkyl)benzene compounds and their derivatives. Included were compounds of the formula

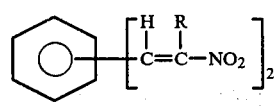

and

-continued

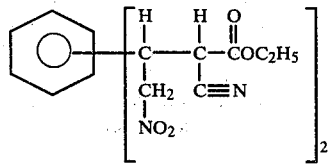

Hedge and coworkers in J. Org. Chem. 26, 3167 (1961) reported that the condensation of a dicarbonyl compound with a very active methylene compound did not produce the 1:4 condensate, but rather only the 1:3 condensate. Thus, when isophthaldehyde and terephthaldehyde were contacted with excess isopropylidinyl malonate in dimethylformamide the product in either case resulted from both an aldol reaction and a Michael reaction at one aldehyde functionality but only an aldol reaction at the remaining aldehyde functionality.

SUMMARY OF THE INVENTION

The invention comprises certain tetracarboxylic acid compounds of the formula

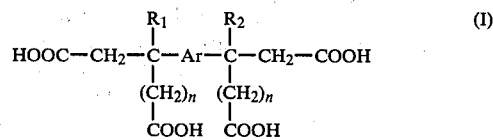

wherein Ar is a $C_{6-20}$ arylene radical selected from the group consisting of:

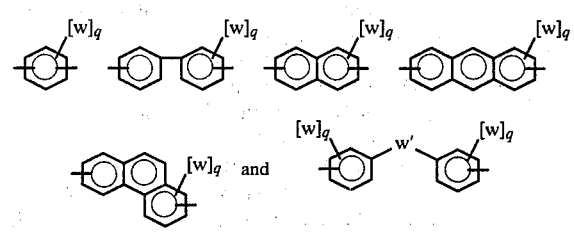

wherein w in each occurrence is halo, nitro, or a $C_{1-10}$ radical selected from alkyl, aryl, alkaryl, aralkyl, haloalkyl, haloaryl, aryloxy and alkoxy; q is an integer from zero to 4; and w' is oxygen, sulfur, alkylene, oxyalkylene, alkylenedioxy or polyoxyalkylene; $R_1$, $R_2$ individually are hydrogen or alkyl, aryl, aralkyl, or alkaryl radicals containing up to 10 carbon atoms, and both n's are zeros or ones. Also included in the invention is a novel process for producing compounds of formula I wherein both n's are 1. The compounds are useful as precursors in the manufacture of polymeric substances. In particular the compounds may be readily converted to stable dianhydrides having 5 or 6 members in each anhydride ring, which thereafter may be reacted with diamine-containing compounds to form unique polyimide compounds which possess improved physical properties at elevated temperatures.

DETAILED DESCRIPTION OF THE INVENTION

The compounds of formula (I) wherein n is zero are prepared by an initial Knovenagel condensation of an alkyl cyanoacetate and an aromatic dicarbonyl compound, either an aromatic dialdehyde or an aromatic diketone. The aromatic diketone may be symmetrical or unsymmetrical. Suitable alkyl cyanoacetate reactants are methyl cyanoacetate, ethyl cyanoacetate, propyl cyanoacetate, butyl cyanoacetate, pentyl cyanoacetate, hexyl cyanoacetate, heptyl cyanoacetate, octyl cyanoacetate, nonyl cyanoacetate, and decyl cyanoacetate. A preferred alkyl cyanoacetate reactant is ethyl cyanoacetate.

Suitable aromatic dicarbonyl compounds are all compounds of the formula

wherein $R_1$, $R_2$ and Ar are as previously defined.

Preferred aromatic dicarbonyl compounds are dialdehyde and diketone derivatives of benzene. Most preferred aromatic dicarbonyl compounds are terephthaldehyde, isophthaldehyde, and p-diacetylbenzene.

The condensation takes place as is known in an inert organic solvent in the presence of a basic catalyst, for example, ethylenediamine, pyridine, piperidine or a buffered catalyst system composed of an amine and the corresponding conjugate acid. Suitable solvents include anhydrous alcohols, e.g., methanol, ethanol, etc. The reaction proceeds smoothly at atmospheric pressure, however, reduced or elevated pressures may also be employed if desired. The condensation may be allowed to proceed at ambient temperature for a sufficient amount of time to produce a precipitate, illustratively about one hour or more. Reaction vessels of ordinary design and construction, e.g., glass flasks may conveniently be used. The product is recovered by filtration or decanting of liquid and may be recrystallized as for example from toluene, benzene or acetone.

The next step of the synthesis is to form the bis-dicyanoester. This may be done in two steps by reacting the bis(2-carbalkoxy-2-cyanoethenyl)arene produced in the initial Knovenagel condensation with an alkali metal cyanide followed by acidification. Alternatively one may contact HCN directly with the bis(2-carbalkoxy-2-cyanoethenyl)arene, as for example by contacting gaseous HCN with the dicyano compound in an inert liquid medium. Again ordinary reaction equipment and parameters may be employed, exercising caution of course when handling the dangerous cyanide reactants.

The bis[(alkoxycarbonyl)dicyanoalkyl]arene compounds are easily recovered as they precipitate from the acidic solution. They may be washed and purified, for example by recrystallization from alcoholic solvents.

Next the bis[(alkoxycarbonyl) dicyanoalkyl]arene compound is subjected to acid hydrolysis. It is not necessary that the bis-dicyano compound be first purified before being subjected to acid hydrolysis, although a recovery and purification step may be employed, if so desired. Preferably, excess concentrated hydrochloric or sulfuric acid is added to the same reaction vessel after the solvent from the above acidification step has been decanted, and the mixture is then refluxed. Because foaming is likely to occur, a defoaming agent should preferably be added to the mixture during the hydrolysis step. I have found a small amount of glacial acetic acid to act as an effective defoaming agent.

Refluxing is continued for several hours, up to ten hours or more. As the reaction progresses, the aromatic bis(dicarboxylic)acid forms and precipitates from solution. The precipitated products are easily recovered, for example, by chilling the solution and then filtering. The compounds may be washed with ice water to remove residual acid and dried under vacuum. Purification by recrystallization may conveniently be accomplished using water as a solvent.

The aromatic tetracarboxylic acid may be used among other utilities as an epoxy curing agent and in the preparation of synthetic resins.

The compounds of formula (I) wherein n is 1 are prepared by an initial Knovenagel condensation of four equivalents of cyanoacetic acid with an aromatic dicarbonyl compound, either an aromatic dialdehyde or an aromatic diketone. The aromatic diketone may be symmetrical or unsymmetrical.

Suitable aromatic dicarbonyl compounds are those compounds previously mentioned. A preferred dicarbonyl compound is terephthaldehyde.

The reactants are combined in at least a 4:1 mole ratio of cyanoacetic acid and aromatic dicarbonyl compound. Preferably, a stoichiometric excess of cyanoacetic acid is present, e.g., the reactants are combined in a mole ratio greater than 4:1.

The condensation takes place in pyridine solvent, preferably in the presence of a catalyst, for example, piperidine. The condensation takes place at an elevated temperature. Preferable are temperatures from about 80° to 200° C., most preferably, from 100° to 150° C. The reaction proceeds smoothly at atmospheric pressure, however, reduced or elevated pressures may also be employed if desired. Reaction times of from several hours to 20 hours or more may be employed. Reaction vessels of ordinary design and construction, e.g., glass flasks may conveniently be used. The resulting product may be recovered by ordinary techniques, for example, by solvent evaporation under reduced pressure, and may be recrystallized if desired.

Next the tetra cyano derivative is hydrolyzed to the tetraacid by refluxing in concentrated acid. It is not necessary that the tetra cyano compound be first purified before being subjected to acid hydrolysis, although a purification step, for example, recrystallization, may be employed if so desired. The acid employed may be concentrated sulfuric or concentrated hydrochloric acid. Because foaming is again likely to occur, a defoaming agent such as glacial acetic acid should preferably be employed.

The reaction conditions and recovery techniques employed are those described previously for the hydrolysis step in producing compounds of formula (I) wherein n is zero.

The tetra acid compound obtained may be recrystallized if desired, although the crude reaction product is generally obtained in sufficiently pure form for further use without a recrystallization step. A suitable solvent for use in recrystallization is a mixture of acetonitrile and dimethylsulfoxide.

SPECIFIC EMBODIMENTS OF THE INVENTION

Having described my invention the following examples are provided as further illustrative of my present invention and are not to be construed as limiting.

EXAMPLE 1 - 1,4-bis(1,2-dicarboxyethyl)benzene

A quantity of 1,4-bis(2-carbethoxy-2-cyanoethenyl)-benzene was prepared according to the method of Perekalin and Lerner. Accordingly, a drop of piperidine was added to quantities to ethyl cyanoacetate and terephthaldehyde in an excess of anhydrous ethanol accompanied by stirring at ambient temperature. A clear solution slowly formed yielding a crystalline condensation product upon further reaction. After 10 hours the condensation was terminated, the precipitate collected by filtration, and washed with methanol. The product, in the form of yellowish-green needles was soluble in hot benzene and acetone but insoluble in ethanol.

Next, 32.4 g (0.1 mole) of this diester was stirred with sodium cyanide (19.6 g, 0.4 mole) in 400 ml of 50 percent aqueous ethanol at ambient temperature, in a 1-liter glass flask. After 1.5 hours the solution was acidified by adding excess concentrated HCl. The product, 1,4-bis(2-carbethoxy-1,2-dicyanoethyl)benzene was deposited as a yellow oil which solidified upon standing.

Next, 200 ml of concentrated hydrochloric acid was added to the decanted reaction flask. Approximately 10 ml of glacial acetic acid was added to inhibit foaming and the mixture was refluxed for 10 hours. A white precipitate gradually formed and separated from the mixture. Refluxing was discontinued and the flask and contents chilled in ice. Filtration followed by washing with ice water and oven drying in vacuo gave 30.1 g (97 percent yield) of 1,4-bis(1,2-dicarboxyethyl)benzene.

To identify the product a small sample was recrystallized from water. Analysis by standard analytical techniques gave the following results:

|  | % C | % H | melting point °C. |
|---|---|---|---|
| calculated | 54.2 | 4.52 | — |
| found | 54.2 | 4.49 | 228–230.5 |

Analysis by nuclear magnetic resonance (NMR) and infrared absorption (IR) spectroscopy also confirmed the product's identity as 1,4-bis(1,2-dicarboxyethyl)benzene.

EXAMPLE 2 - 1,3-bis(1,2-dicarboxyethyl)benzene

A mixture of isophthaldehyde (2.68 g, 0.02 mole), ethyl cyanoacetate (4.6 g, 0.04 mole), piperidine (2 drops) and anhydrous methanol (50 ml) was stirred at room temperature for 5.5 hours. A white precipitate (5.5 g, 85 percent yield) was collected and identified as 1,3-bis(2-carbethoxy-2-cyanoethenyl)benzene.

The above-prepared product (5.1 g, 0.015 mole) was suspended in 75 ml water. Sodium cyanide (2.36 g, 0.048 mole) was added with stirring at ambient temperature. After 2 hours the clear solution was acidified and the product extracted with methylene chloride. This fraction was washed with water, dried with anhydrous MgSO₄ and then evaporated to dryness yielding 5.1 g of a waxy white solid. Analysis by IR and NMR spectroscopy confirmed the product's identity as 1,3-bis(2-carbethoxy-1,2-dicyanoethyl)benzene.

The product was then hydrolyzed according to the same procedure employed in Example 1. The resulting product, 1,3-bis(1,2-dicarboxyethyl)benzene, was identified by IR and NMR spectroscopy.

EXAMPLE 3 -
1,4-bis(1,2-dicarboxy-1-methylethyl)benzene

A mixture of p-diacetylbenzene (20.25 g, 0.125 mole), ethyl cyanoacetate (28.3 g, 0.25 mole), ammonium acetate (3.85 g) and acetic acid (10 g) was combined in a 500 ml glass round-bottom flask with toluene (150 ml) and refluxed for 12 hours. A Dean-Stark trap was employed to trap water formed during the reaction. Refluxing was discontinued and the solvent evaporated. The residue containing crude product was distilled under reduced pressure. One fraction, boiling point range 177° C.–195° C. (0.6 mm) amounting to 20.6 g was identified as predominately the 1:1 condensation product. A second fraction, boiling point ~200° C. yielded 18.2 g of 1,4-bis(2-carbethoxy-2-cyano-1-methylethenyl)benzene.

A portion of this second product weighing 9.29 g was heated at 85° C. for 2 hours in 50 ml water having dissolved therein sodium cyanide (5.12 g). After heating, the solution was stirred for 3 hours at room temperature. The diester slowly dissolved resulting in a clear light yellow solution. The solution was then acidified with excess concentrated HCl and the product extracted with chloroform. The product, 1,4-bis(2-carbethoxy-1,2-dicyano-1-methylethyl)benzene was identified by IR and NMR spectroscopy.

The product was then hydrolyzed by refluxing according to the procedure of Example 1 above. The product, 1,4-bis(1,2-dicarboxy-1-methylethyl)benzene, was identified by IR and NMR spectroscopy.

EXAMPLE 4 - 1,4-bis-2-(1,3-dicarboxy)propyl benzene

Terephthaldehyde (53.6 g, 0.4 mole) and cyanoacetic acid (170 g, 2 moles) were combined in a round bottom flask with 350 ml of pyridine containing 20 ml piperidine. The mixture was then refluxed for about 15 hours. A yellow solution remained when refluxing ceased. After the solvent was removed by evaporation under reduced pressure a residue remained. This residue was washed with aqueous HCl followed by methanol and the product dried leaving 84.5 g (80.6% yield) of 1,4-bis-2-(1,3-dicyano)propyl benzene.

A portion of the product was hydrolyzed by adding the tetracyano compound to 200 ml concentrated HCl having added thereto 50 ml glacial acetic acid to inhibit foaming in a glass round bottom flask. Heating was commenced and the mixture refluxed for about 9 hours.

The product obtained upon chilling and filtration of the acid solution followed by washing with ice water had a melting point range of 256°–258° C. Yield was 68 g or 100 percent.

An analytic sample was recrystallized from acetonitrile-dimethyl sulfoxide solution. The recrystallized product had the following analysis:

|  | % C | % H | melting point °C. |
|---|---|---|---|
| calculated | 56.8 | 5.33 | — |
| found | 57.0 | 5.38 | 257–259 |

Analysis by IR and NMR spectroscopy confirmed the product's identity as 1,4-bis-2-(1,3-dicarboxy)propylbenzene.

EXAMPLE 5 -
1,3-bis[4-(1,2-dicarboxyethyl)phenoxy]propane

The aldehyde, 1,3-bis(4-formylphenoxy)propane, was prepared by refluxing p-hydroxybenzaldehyde and 1,3-dibromopropane in an aqueous caustic solution. The recovered and recrystallized product (14.2 g, 0.05 mole) was combined with ethyl cyanoacetate (11.3 g, 0.1 mole) in methanol (100 ml) and about 1.0 ml of piperidine catalyst added. The mixture was stirred at room temperature for 24 hours resulting in the formation of white, solid precipitate.

Recovery by filtration and washing with methanol gave 21.1 g (89 percent yield) of the desired product, 1,3-bis[4-(2-carbethoxy-2-cyanoethenyl)phenoxy]propane. The structure was confirmed by NMR and IR analysis.

The desired tetracyanide derivative was formed by adding 100 ml of 2 molar aqueous NaCN to a mixture of the above compound (46.0 g, 0.097 mole), triethylamine (7 g) and ethanol (70 ml). The resulting mixture was stirred for 1⅓ hours at 50° C. until the solid biscyanoethenyl ester had dissolved. Upon acidification the desired product separated and was recovered.

This solid was added to 250 ml of concentrated HCl and the mixture refluxed for about 10 hours to effect hydrolysis and decarboxylation. The desired tetracarboxylic acid was isolated by filtration after cooling in an ice bath. Yield was 22.0 g (49 percent).

The product was a tan colored solid. A sample recrystallized from water melted at 221° C.–223° C. Analysis by NMR and IR confirmed the product's identity as 1,3-bis-[4-(1,2-dicarboxyethyl)phenoxy]propane.

EXAMPLE 6 - Polyimide Polymer Formation

A quantity of the product of Example 1, 1,4-bis(1,2-dicarboxyethyl)benzene was converted to the corresponding dianhydride, 1,4-bis(tetrahydrofuran-2,5-dion-3-yl)benzene by refluxing in acetic anhydride solvent for about 2 hours. The acetic anhydride was evaporated under reduced pressure and the residue collected. Recrystallization from methylethylketone gave the dianhydride which was characterized by infrared and nuclear magnetic resonance spectroscopy.

The polyimide was next produced by reacting a small quantity of 1,4-bis(tetrahydrofuran-2,5-dion-3-yl)benzene (2.74 g, 0.01 mole) with 4,4'-oxydianiline (2.0 g, 0.01 mole) in a mixture of 27 ml of m-cresol and 8 ml of toluene in a glass flask. Approximately 1 ml of triisopentylamine catalyst was added and the reaction mixture heated to about 180° C. After about 2 hours a completely homogenous mixture resulted.

The polyimide was isolated by precipitating in acetone. A white, fibrous polyimide-containing polymer was recovered (4.1 g, 94 percent yield). The inherent viscosity as measured in N-methylpyrrolidinone (25° C., 0.5 g/dl) was 0.69. The glass transition temperature as determined by differential scanning calorimetry was determined to be 275° C.

What is claimed is:

1. A tetracarboxylic acid compound of the formula

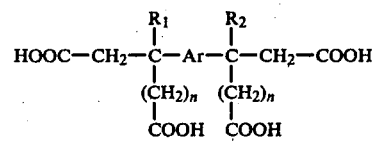

wherein Ar is a $C_{6-20}$ arylene radical selected from the group consisting of:

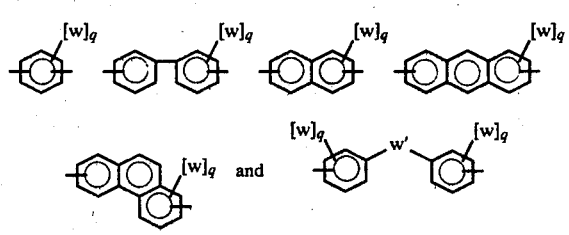

wherein w in each occurrence is halo, nitro, or a $C_{1-10}$ radical selected from alkyl, aryl alkaryl, aralkyl, haloalkyl, haloaryl, aryloxy and alkoxy; q is an integer from zero to 4; and w' is oxygen, sulfur, alkylene, oxyalkylene, alkylenedioxy, or polyoxyalkylene; $R_1$, $R_2$ individually are hydrogen or alkyl, aryl, aralkyl, or alkaryl radicals containing up to 10 carbon atoms; and both n's are zeros or ones.

2. A compound according to claim 1 wherein Ar is a phenylene radical.

3. A compound according to claim 2 that is 1,4-bis(1,2-dicarboxy-1-methylethyl)benzene.

4. A compound according to claim 2 wherein $R_1$ and $R_2$ are hydrogen.

5. A compound according to claim 4 that is 1,4-bis(1,2-dicarboxyethyl)benzene.

6. A compound according to claim 4 that is 1,3-bis(1,2-dicarboxyethyl)benzene.

7. A compound according to claim 4 that is 1,4-bis-2-(1,3-dicarboxypropyl)benzene.

8. A compound according to claim 4 that is 1,3-bis[4-(1,2-dicarboxyethyl)phenoxy]propane.

* * * * *